(12) United States Patent
Weyl et al.

(10) Patent No.: US 6,487,890 B1
(45) Date of Patent: Dec. 3, 2002

(54) LAMBDA PROBE HAVING A PREFORMED, VENTILATED TUBE

(75) Inventors: Helmut Weyl, Schwieberdingen (DE); Bernhard Wild, Markgroeningen (DE); Peter Dettling, Waiblingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/368,844

(22) Filed: Aug. 5, 1999

(30) Foreign Application Priority Data

Aug. 5, 1998 (DE) .......................................... 198 35 345

(51) Int. Cl.[7] .............................................. G01N 27/00
(52) U.S. Cl. ...................................................... 73/23.31
(58) Field of Search ............................. 73/23.31, 23.32; 204/428; 338/34; 422/88, 98

(56) References Cited

U.S. PATENT DOCUMENTS

| | | | | |
|---|---|---|---|---|
| 3,996,007 A | * | 12/1976 | Fang et al. ............. | 23/253 TP |
| 4,228,128 A | * | 10/1980 | Esper et al. ................... | 422/98 |
| 5,031,445 A | * | 7/1991 | Kato et al. ................. | 73/23.31 |
| 5,246,562 A | * | 9/1993 | Weyl et al. ................. | 204/424 |
| 5,499,528 A | * | 3/1996 | Bahar ......................... | 73/23.2 |
| 5,522,980 A | * | 6/1996 | Hobbs et al. ............... | 204/432 |
| 5,708,213 A | * | 1/1998 | Batey ....................... | 73/861.12 |
| 5,711,863 A | * | 1/1998 | Henkelmann et al. ...... | 204/428 |
| 5,719,340 A | * | 2/1998 | Poortmann et al. ....... | 73/861.08 |
| 5,800,689 A | * | 9/1998 | Hori et al. .................. | 204/428 |
| 5,874,664 A | * | 2/1999 | Watanabe et al. .......... | 73/23.32 |
| 5,955,656 A | * | 9/1999 | Graser et al. .............. | 73/23.31 |
| 6,018,982 A | * | 2/2000 | Friese et al. ................. | 73/23.2 |
| 6,178,806 B1 | * | 1/2001 | Watanabe et al. .......... | 73/23.32 |

FOREIGN PATENT DOCUMENTS

DE          40 15 486          11/1990

* cited by examiner

Primary Examiner—Hezron Williams
Assistant Examiner—Charles D. Garber
(74) Attorney, Agent, or Firm—Kenyon & Kenyon

(57) ABSTRACT measuring sensor, in particular for determining the oxygen content in the exhaust gases of internal combustion engines, includes a sensor element which is axially arranged in a metallic housing and which is contacted by at least one connecting cable, which is brought axially out of the housing, through a support sleeve member, and which has a cable insulation, a reference atmosphere for the sensor element being introducible into the housing, and the cable insulation, at the surface area, having, at least in certain regions, at least one gas-permeable section, such that the reference atmosphere arrives inside the cable insulation and, from there, in the housing. The gas-permeable region of the cable insulation is directly contiguous to the cable-output end of the support-sleeve member and sheathed there by a porous tube of gas-permeable PTFE material, while allowing for a radial clearance between the porous PTFE tube and the gas-permeable section of the cable insulation.

8 Claims, 1 Drawing Sheet

LAMBDA PROBE HAVING A PREFORMED, VENTILATED TUBE

FIELD OF THE INVENTION

The present invention relates to a measuring sensor, in particular for determining the oxygen content in the exhaust gases of internal combustion engines, having a sensor element which is axially arranged in a metallic housing and which is contacted by at least one connecting cable, which is brought axially out of the housing, through a support sleeve member, and which has a cable insulation, a reference atmosphere for the sensor element being introducible into the housing, and the cable insulation, at the surface area, having, at least in certain regions, at least one gas-permeable section, such that the reference atmosphere arrives inside the cable insulation and, from there, in the housing.

BACKGROUND INFORMATION

A measuring sensor or a λ-probe is known from German Patent No. 196 31 501. In the known measuring sensor, the connecting cable insulation is at least somewhat porous over a certain section. The openings placed in the connecting cable insulation are covered by an additional porous PTFE film, to protect them from external contamination. This forms a continuous air-exchange channel between the measuring sensor and the external air. This design approach is relatively economical, since it does not necessitate any additional outlay with respect to the number of components used. However, adhering precisely to a defined porosity is difficult.

From other λ-probes, one knows of design approaches where Gore-Tex (porous PTFE film, which is permeable to air, but is impermeable to water and oil, and is fabricated using a special process of the firm Gore) is used directly at the cable output of the measuring sensor. These known design approaches require a relatively substantial outlay for design integration, but hardly provide protection from contamination caused by street dirt, oil, undersea coatings, inter alia, and, moreover, they limit the maximum thermal loading capacity at the cable output of the probe.

SUMMARY OF THE INVENTION

An object of the present invention is to provide a measuring sensor, in particular a measuring sensor suited for use as a λ-probe, having a "ventilation section" situated at a relatively cold location of the measuring sensor, and which will make it possible to minimize changes in porosity caused by temperature variations and external contamination.

By providing for the gas-permeable region of the cable insulation to be directly contiguous to the cable-output end of the support-sleeve member and to be sheathed there by a porous tube of gas-permeable PTFE material, while allowing for a radial clearance between the porous PTFE tube and the gas-permeable section of the cable insulation, the present invention not only ensures an optimal ingress of air, i.e. ingress of reference atmosphere to the inside the cable insulation, but also facilitates integration of the porous tube of gas-permeable PTFE material, using relatively simple means, at this relatively cold end of the measuring sensor.

To ensure the radial clearance between the porous PTFE tube and the cable insulation, an inner collet (clamp-type sleeve) is situated between the cable insulation and the porous PTFE tube, and surrounds the cable insulation with radial clearance. This collet has at least one transverse bore in the gas-permeable section of the cable insulation, thereby ensuring free admission of air to the gas-permeable section of the cable insulation.

At this point, the porous PTFE tube is preferably attached to the support-sleeve member and to the inner collet by providing an outer collet surrounding the support-sleeve member and the inner collet with rounded, tamped-out sections at an axial distance, to form a keyed connection (using form locking) between the porous PTFE tube and the cable-output end of the support-sleeve member. These rounded, tamped-out sections of the outer collet define a radial bulge of a specific length, ensuring a free supply of air to a defined length of the porous PTFE tube. In the bulge region, the outer collet has at least one transverse bore which is able to be aligned with the transverse bore in the inner collet. A preformed PTFE tube which protects the cable from breakage and the influences of temperature can be simply integrated at the probe outlet in that the tamped-out section at the cable-output end of the outer collet wedges the preformed PTFE tube radially between the porous PTFE tube and the inner collet.

To provide further protection from external contamination, the "ventilated section", i.e. the bulge of the outer collet, is able to be sheathed by a silicon-coated, woven-glass tube, which covers the transverse bore or transverse bores in the outer collet, protecting it/them from external contamination. This likewise minimizes any change in the porosity properties of the ventilated section over the service life of the measuring sensor.

Gore-Tex, which, as already mentioned, is fabricated from a porous PTFE film, using a special process of the firm Gore, is preferably used for the porous PTFE tube, as it is permeable to air, but is impermeable to water and oil. One can select the appropriate Gore-Tex quality to adapt the breathability to the requirements of the measuring sensor, within a broad range and with minimal divergence. Thus, for example, contaminant residues resulting from the manufacturing process are able to be easily eliminated using porous membranes, a smaller porosity being advantageous in the case of a more serious risk of contamination, for example from gasoline, engine cleaners, and the like. The inner and outer collets can preferably be made of metal, in particular of stainless steel, and the support-sleeve member of silicon material.

BRIEF DESCRIPTION OF THE DRAWING

The FIGURE depicts a schematic, truncated longitudinal section of the cable-output end of an exemplary embodiment of the measuring sensor according to the present invention.

DETAILED DESCRIPTION

Figure 1:
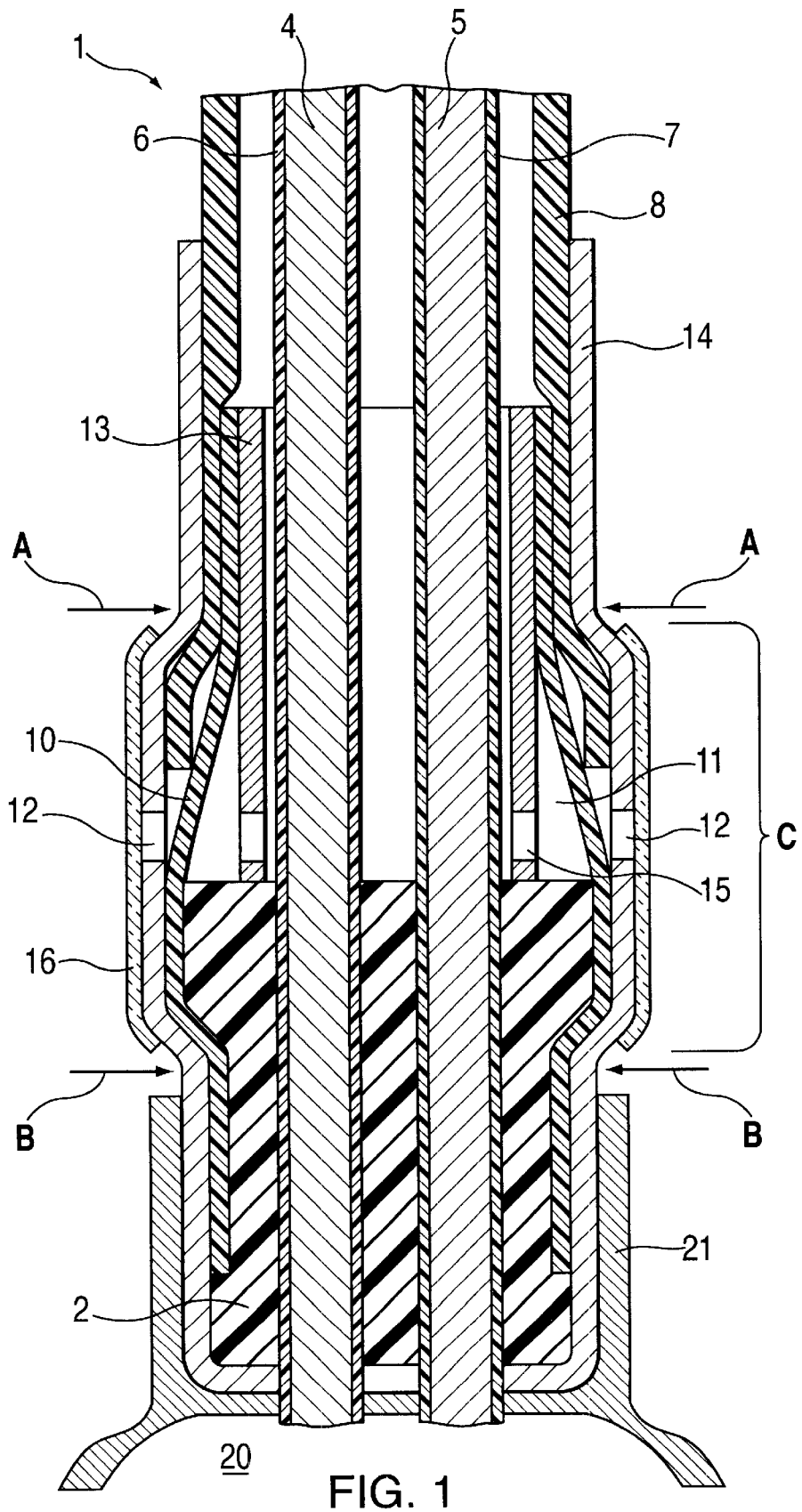

In the FIGURE, the measuring sensor is denoted by reference numeral 1. Illustrated in the FIGURE are two connecting cables 4 and 5, which are routed through a collet/support-sleeve member 2 at the cable-output end of the measuring sensor. The sensor element 20 of the measuring sensor is indicated at the bottom of the measuring sensor shown in the FIGURE. The metallic housing 21 which surrounds the sensor element 20 and which is attached at the bottom end of measuring sensor 1 in the FIGURE is partially shown. Where they are joined to collet/support-sleeve member 2, cable insulations 6, 7 have a gas-permeable region for introducing a reference atmosphere for the sensor element into the housing. There, an inner collet 13 is slid over cable insulations 6, 7, while maintaining a radial clearance, and has at least one transverse bore 15 in the section directly adjoining collet/support-sleeve member 2 (two transverse bores 15 are shown in the FIGURE). This inner collet 13 made of metal, in particular of stainless steel is used, first of all, to keep a porous tube 10 of gas-permeable PTFE material (Gore-Tex) covering the gas-permeable section of cable insulation 6, 7 at a radial distance from cable insulations 6, 7, permitting a free passage of air through porous tube 10, through an air gap 11, then through transverse bores 15 of inner collet 13, and through the gas-permeable sections of cable insulations 6, 7, to the inside of the same. As the FIGURE shows, porous tube 10 of gas-permeable PTFE material overlaps collet/support-sleeve member 2 and terminates at the top with the inner collet 13.

As the FIGURE also shows, an outer collet 14 is slid over the entire ventilation section and collet/support-sleeve member 2, which, for air supply purposes, likewise has one or more transverse bores 12 (two transverse bores 12 are shown in the FIGURE). To enable all components to be joined to one another in a solid and gas-tight manner, outer collet 14 is tamped out in a rounded fashion at the front, i.e. measuring-gas-side end, and at the rear, i.e., cable-output-side end. This is illustrated by arrows A and B.

the vicinity of the ventilation section, the axially spaced apart, rounded, tamped-out sections A, B of outer transverse collet (sleeve) 14 form a radial bulge C of a specific length, to ensure a free supply of air to a defined axial length of the gas-permeable PTFE tube 10. During the tamping operation, the sealing collet/support-sleeve member 2, made of silicon, depicted on the bottom side of the FIGURE, is imperviously joined, with the greatest possible form locking, to gas-permeable PTFE tube 10, and collet/support-sleeve member 2 is joined sealingly with force locking to connecting cables 4, 5. In addition, the upper rounded, tamped-out section A presses PTFE preformed tube 8, which protects connecting cables 4, 5 and the subjacent gas-permeable PTFE tube, against inner collet 13. Inner collet 13 is easily shaped during the tamping operation. Since during the tamping operation, inner collet 13 is likewise able to come to rest imperviously on the silicon collet/support-sleeve member 2, transverse bores 15 of the inner collet in the region of bulge C are required for the passage of air. To ensure with certainty the supply of air to the inside of the housing, a PTFE sleeve (not shown) of the probe can itself have a blind bore (likewise not shown) in parallel to the cable feed-through bores.

An outer, silicon-coated, woven-glass tube 16, which offers an optimal protection for transverse bores 12 of outer collet 14 and of porous tube 10, which is subjacent thereto, from external contamination, is slid over bulge C.

Contaminant residues resulting from the manufacturing process are able to be eliminated more easily when porous material is used for PTFE tube 10, while a smaller porosity of tube 10 is advantageous in the case of heavier contamination, for example from gasoline and engine cleaners. Thus, by selecting the appropriate Gore-Tex quality for porous tube 10, one is able to adapt its breathability and resistance to contamination to the requirements of the measuring sensor, within a broad range and with minimal divergence.

What is claimed is:

1. A measuring sensor comprising:

a metallic housing;

a sensor element axially situated in the housing;

a support-sleeve member having a cable-output end;

at least one connecting cable contacting the sensor element, the at least one connecting cable extending axially out of the housing through the support-sleeve member, the at least one connecting cable having a cable insulation, the cable insulation having at least one gas-permeable section at a surface area, a reference atmosphere for the sensor element being introducible inside the cable insulation and into the housing, the gas permeable section of the cable insulation being directly contiguous to the cable-output end of the support-sleeve member; and a porous tube composed of gas-permeable PTFE material sheathing the gas-permeable section of the cable insulation, a radial clearance being defined between the porous tube and the gas-permeable section of the cable insulation.

2. The measuring sensor according to claim 1, wherein the measuring sensor is for determining an oxygen content in exhaust gases of an internal combustion engine.

3. The measuring sensor according to claim 1, further comprising an inner collet for ensuring the radial clearance, the inner collet being situated between the cable insulation and the porous tube, the inner collet surrounding the cable insulation with the radial clearance, the inner collet having at least one transverse bore in the gas-permeable section.

4. The measuring sensor according to claim 3, further comprising an outer collet surrounding the support-sleeve member, the outer collet and the inner collet having rounded, tamped-out sections situated at a preselected axial spacing, the porous tube being attached to the cable-output end of the support-sleeve member in a keyed connection.

5. The measuring sensor according to claim 4, wherein the axial spacing of the sections of the outer collet defines a radial bulge of a preselected length, to ensure a free supply of air to a defined length of the porous tube.

6. The measuring sensor according to claim 5, wherein the outer collet has at least one transverse bore in a region of the radial bulge.

7. The measuring sensor according to claim 6, further comprising a preformed PTFE tube sheathing the connecting cables over a portion of a length of the connecting cables between the porous tube and the inner collet, a section of the outer collet sealingly wedging the preformed PTFE tube.

8. The measuring sensor according to claim 6, further comprising a silicon-coated, woven-glass tube sheathing the outer collet in the region of the radial bulge, the tube protecting the at least one transverse bore from an external contamination.

\* \* \* \* \*

UNITED STATES PATENT AND TRADEMARK OFFICE
CERTIFICATE OF CORRECTION

PATENT NO.   : 6,487,890 B1
DATED        : December 3, 2002
INVENTOR(S)  : Weyl et al.

It is certified that error appears in the above-identified patent and that said Letters Patent is hereby corrected as shown below:

Title page,
Item [57], ABSTRACT, change "measuring sensor" to -- A measuring sensor , --

Column 3,
Line 23, change "the vicinity" to -- In the vicinity --

Column 4,
Line 28, change "3. The measuring sensor…...the gas-permeable section." to -- 3. A measuring sensor, comprising:
   a metallic housing ;
   a sensor element axially situated in the housing;
   a support-sleeve member having a cable-output end;
   at least one connecting cable contacting the sensor element, the at least one connecting cable extending axially out of the housing through the support-sleeve member, the at least one connecting cable having a cable insulation, the cable insulation having at least one gas-permeable section at a surface area, a reference atmosphere for the sensor element being introducible inside the cable insulation and into the housing, the gas permeable section of the cable insulation being directly contiguous to the cable-output end of the support-sleeve member;
   a porous tube composed of gas-permeable PTFE material sheathing the gas-permeable section of the cable insulation, a radial clearance being defined between the porous tube and the gas-permeable section of the cable insulation; and
   an inner collet for ensuring the radial clearance, the inner collet being situated between the cable insulation and the porous tube, the inner collet surrounding the cable insulation with the radial clearance, the inner collet with the radial clearance, the inner collet having at least one transverse bore in the gas-permeable section. --

Signed and Sealed this

Twenty-seventh Day of July, 2004

JON W. DUDAS
*Acting Director of the United States Patent and Trademark Office*